United States Patent [19]

Sawyer

[11] Patent Number: 5,108,417
[45] Date of Patent: Apr. 28, 1992

[54] ANTI-TURBULENT, ANTI-THROMBOGENIC INTRAVASCULAR STENT

[75] Inventor: Philip N. Sawyer, Brooklyn, N.Y.

[73] Assignee: Interface Biomedical Laboratories Corp., Brooklyn, N.Y.

[21] Appl. No.: 583,882

[22] Filed: Sep. 14, 1990

[51] Int. Cl.$^5$ .............................................. A61B 17/00
[52] U.S. Cl. .................................... 606/198; 606/191; 623/1
[58] Field of Search ................ 606/191, 198, 153–156; 623/1

[56] References Cited

U.S. PATENT DOCUMENTS

| | | | |
|---|---|---|---|
| 3,667,069 | 6/1972 | Blackshear et al. | 623/3 |
| 3,868,956 | 3/1975 | Alfidi et al. | 128/345 |
| 4,441,215 | 4/1987 | Kaster | 623/1 |
| 4,503,569 | 3/1985 | Dotter | 3/1.4 |
| 4,512,338 | 4/1985 | Balko et al. | 128/1 R |
| 4,553,545 | 11/1985 | Maass et al. | 128/341 |
| 4,560,374 | 12/1985 | Hammerslag | 604/49 |
| 4,580,568 | 4/1986 | Gianturco | 128/345 |
| 4,649,992 | 3/1987 | Wiktor | 128/344 |
| 4,665,918 | 5/1987 | Garza et al. | 128/343 |
| 4,681,110 | 7/1987 | Wiktor | 128/343 |
| 4,690,684 | 9/1987 | McGreevy et al. | 623/12 |
| 4,733,665 | 3/1988 | Palmaz | 128/343 |
| 4,739,762 | 4/1988 | Palmaz | 128/343 |
| 4,753,236 | 6/1988 | Healey | 128/334 R |
| 4,760,849 | 8/1988 | Kropf | 128/341 |
| 4,768,507 | 9/1988 | Fischell et al. | 128/303 |
| 4,770,176 | 9/1988 | McGreevy et al. | 128/334 R |
| 4,795,458 | 1/1991 | Regan | 623/1 |
| 4,800,882 | 1/1989 | Gianturco | 128/343 |
| 4,830,003 | 5/1989 | Wolff et al. | 128/343 |
| 4,878,906 | 11/1989 | Lindemann et al. | 623/1 |
| 4,886,062 | 12/1989 | Wiktor | 128/343 |
| 4,986,831 | 1/1991 | King et al. | 623/1 |

OTHER PUBLICATIONS

Sawyer et al, "Possible Relationship of Ionic Structure of the Blood-Intimal Interface to Intravascular Thrombosis," *Surgery*, vol. 56, No. 4, pp. 846–854 (1964).
Dotter, "Transluminally Placed Coilspring Endoarterial Tube Grafts," *Investigative Radiology*, vol. 4, p. 329 (1969).
Sugita et al, "Nonsurgical Implantation of a Vascular Ring Prosthesis Using Thermal Shape Memory Ti/Ni Alloy (Nitionl Wire)," *Trans. Amer. Soc. Artif. Intern. Organs*, vol. 23, pp. 30–34.
Cragg et al, "Nonsurgical Placement of Arterial Endoprosthesis: A New Technique Using Nitinol Wire," *Radiology*, vol. 147, pp. 259–260 (1983).
Sutton et al, "Vascular Stenting in Normal and Atheroschlerotic Rabbits," pp. 667–683 (1989).
Schatz, "A View of Vascular Stents," *Circulation*, vol. 79, No. 2, 445–457 (1989).
Rollins et al, "Self-Expanding Metallic Stents: Preliminary Evaluation in an Atherosceleratic Model," *Radiology*, vol. 163, pp. 739–742, 1987.
Sutton et al, "Titanium-Nickel Intravascular Endoprosthesis," *AJR*, vol. 151, pp. 597–601, 1988.
Oku et al, "A Titanium-Nickel Alloy Intravascular Endoprosthesis," *Trans. Amer. Soc. Artif. Intern. Organs*, vol. 23, pp. 399–403 (1988).
Wright et al, "Percutaneous Endovascular Stents: An Experimental Evaluation," *Radiology*, vol. 156, pp. 69–72 (1985).
Palmaz et al, "Expandable Intraluminal Vascular Graft: A Feasibility Study," *Surgery*, pp. 199–205 (1986).
Cragg et al, "Percutaneous Arterial Grafting," *Radiology*, vol. 150, pp. 45–49 (1984).
Tominaga et al, "Intravascular Endoprostheses," *Trans. Amer. Soc. Artif. Intern. Organs*, vol. 23, pp. 376–378 (1989).

(List continued on next page.)

Primary Examiner—Michael H. Thaler
Attorney, Agent, or Firm—Pennie & Edmonds

[57] ABSTRACT

An anti-turbulent, anti-thrombogenic intravascular stent of a helically shaped titanium or aluminum strip having an airfoil on internal surfaces thereof for increasing blood flow velocity through the stent without creating areas of stagnant or turbulent flow therein.

8 Claims, 1 Drawing Sheet

OTHER PUBLICATIONS

Sigwart et al, "Intravascular Stents To Prevent Occlusion and Restenosis After Transluminal Angioplasty," *N.E. Jour. Med.*, vol. 316, No. 12, pp. 701-706 (1987).

Maass et al, "Radiological Follow-up of Transluminally Inserted Vascular Endoprostheses: An Experimental Study Using Expanding Spirals," *Radiology*, vol. 152, No. 3, pp. 659-663 (1984).

Sawyer et al, "Long-Term Patency of Solid-Wall Vascular Prostheses," *Arch. Surg.*, vol. 91, pp. 735-742 (1965).

Harshaw et al, "The Ionic Structure Of the Blood Intimal Interface as an Aid in the Development of Vascular Prostheses," *Trans. Amer. Soc. Artif. Organs*, vol. 9, pp. 317-320 (1963).

Sawyer et al, "Ionic Architecture at the Vascular Wall Interface," *Trans. Amer. Soc. Artif. Organs*, vol. 10, pp. 316-319 (1964).

Sawyer et al, "Irreversible Electrochemical Precipitation of Mammalian Platelets and Intravascular Thrombosis," *Nat. Acad. Sci.*, vol. 53, No. 1, pp. 200-207 (1965).

Wu et al, "Effect of Various Metal Electrode Sutures in the Production of Increased Tensile Strength of Wounds," *Surgical Forum*, vol. 16, pp. 89-91 (1965).

Sawyer et al, "Electrochemical Criteria in the Choice of Materials Used in Vascular Prosthesis," *Biophysical Mechanics in Vascular Homeostasis and Intravascular Thrombosis* (P. N. Sawyer, editor) Appleton-Century-Crofts, N.Y., N.Y., pp. 337-348, 1967.

Wu et al, "The Use of Various Metal Sutures to Increase Tensile Strength of Wounds," *Surgery*, vol. 61, No. 2, pp. 242-247 1987.

Sawyer et al, "Electrochemical Precipitation of Blood Cells on Metal Electrodes: an Aid in the Selection of Vascular Prostheses?", *Proceedings of the National Academy of Sciences*, vol. 53, No. 2, pp. 194-300, 1965.

Boddy et al, "Some Electrochemical Properties of Solid-Liquid Interfaces and the Electrode Behavior or Erythrocytes," *Biophysical Mechanics in Vascular Homeostasis and Intravascular Thrombosis* (P. N. Sawyer, editor) Appleton-Century-Crofts, N.Y., N.Y., pp. 30-41, 1967.

Chopra et al, "Relation Between Thrombosis on Metal Electrodes and the Position of Metal in Electromotive Series," *Nature*, vol. 215, No. 5109, p. 1494, Sep. 1967.

Wu et al, "Effect of Aluminum Suture on Wound Healing: Long Term Comparative Study on the Tensile Strength and Hydroxyproline Content," *Surgery*, vol. 64, No. 3, pp. 605-609, 1968.

Lucas et al, "Nonthrombogenic AC Polarized Copper Prosthesis," *Biomat. med. Der. Art. Org.*, vol. 3, No. 2, pp. 215-232 (1975).

Srinivasan et al., "Thrombosis on Metal Surfaces—Relationship to Position of Metal in the Electromative Series and Metal Blood Interface Potential," *The Physiologist*, vol. 10, No. 3, Aug. 1967.

Sawyer et al, "Electrical Potential Differences Across the Normal Aorta and Aortic Grafts of Dogs," *Amer. J. Physiol.* 175:113, 1953.

Sawyer et al, "Bioelectric Phenomena as an Etiologic Factor in Intravascular Thrombosis," *Surg.*, 34:491, 1953.

Sawyer et al, "The Experimental Use of Oriented Electric Fields to Delay and Prevent Intravascular Thrombosis," Surg. Forum, *Amer. Col. Surg. Forum, Amer. Col. Surg.*, W. B. Saunders, Phila., 6:173, 1955.

Sawyer et al, "Application of Gas Endarterectomy to Atherosclerotic Peripheral Vessels and Coronary Arteries: Clinical and Experimental Results," *Circulation*, Suppl. 1, 35, 36:I-163, 1967.

Dotter et al, "Transluminal Iliac Artery Dilatation. Nonsurgical Treatment of Atheromatous Narrowing," *JAMA*, 230, 117-24, 1974.

Gruentzig et al, "Current Status of Dilatation Catheter and Guiding Systems," *Amer. J. Cardiology*, 53:92-93C, 1984.

Sawyer et al, "Characteristics of the Human Heart: Design Requirements for Replacement," *Trans. ASAIO*, 17:470, 1971.

Sawyer et al, "Significance of Electrochemical Phenomena in Intravascular Thrombosis," *Nature*, 206:1162, 1965.

ANTI-TURBULENT, ANTI-THROMBOGENIC INTRAVASCULAR STENT

FIELD OF THE INVENTION

This invention relates to an intravascular stent to maintain vascular patency in humans and animals. Also, the invention relates to a means for reducing the risk of thrombosis due to the implanted stent.

BACKGROUND OF THE INVENTION

Intravascular stents have long been applied to maintain vascular patency. Intravascular stents are used in conjunction with balloon angioplasty wherein a balloon is inflated to expand a constricted vessel in order to restore proper blood flow. The intravascular stent is then positioned inside the now expanded vessel to ensure the vessel maintains the enlarged diameter.

However, attempts to develop a prosthetic stent which would hold open a blood vessel and not develop transluminal thrombus have enjoyed limited long term success. There has been very little significant improvement with the exception of an effort to create a more expansible metallic stent.

For a metallic stent to satisfy the limits for antithrombogenesis while simultaneously maintaining the lumen of a blood vessel in which the stent has been placed, the stent has to fulfill the electrochemical laws for thrombosis. That is, the stent has to maintain a potential difference more negative than plus 250 millivolts versus the normal hydrogen electrode. In addition, the stent must exhibit limited corrosion and limited tissue destruction over the duration of the stent life. It was found very early on that while some of the metals on the corrosive side of the electromotive series would maintain a very negative potential, many of these metals upon ionizing and going into solution produced cellular destruction due to tissue and cellular toxicity. For this reason, the number of materials which can be used to develop a metallic implantable intravascular stent is limited to four or five metals that are known to be antithrombogenic and anticorrosive. The most useful of these appears to be titanium or aluminum.

Titanium and aluminum produce a non-soluble surface oxide on exposure to blood and tend not to go into solution. In addition, titanium and aluminum develop a very negative potential with reference to the normal hydrogen electrode. Titanium and aluminum deposit almost no coagulant materials, coagulant enzymes, or proteins.

A number of patents have been found describing various stent designs as well as methods for delivery of the stent to the desired position in the vessel. These patents include:

U.S. Pat. Nos. 3,868,956 and 4,503,569, each of which describes methods wherein a stent comprising a temperature responsive device is implanted in the damaged vessel and thereafter expanded by means of an external heat source.

U.S. Pat. No. 4,553,545, which discloses a method whereby a complex mechanical rotating device and coaxial cables are employed to increase the diameter of the implanted stent.

U.S. Pat. No. 4,580,568, which describes a stent wherein a single wire forming a closed loop is expanded in the damaged vessel to maintain vascular patency. The loop of wire is compressed to form a series of straight segments and bands, wherein said bends store energy in the compressed state. Upon removal of a compression means the stent expands and exhibits a circular configuration.

U.S. Pat. No. 4,649,992, which describes a device in combination with a catheter which is a compression spring retained by a partially inflated balloon and an abutment immediately behind the balloon on the catheter shaft. The spring prosthesis is transported in this manner to the desired location and released by totally evacuating said balloon thereby allowing the spring prosthesis to expand linearly.

U.S. Pat. No. 4,681,110, which describes a catheter for delivery of a stent comprising woven plastic strands forming a tube which can be compressed radially. The orientation of the plastic strands provide the resilience for tube to expand from the compressed state.

U.S. Pat. No. 4,768,507, which discloses a catheter comprising an outer cylinder and inner core, wherein said inner core comprises spiral grooves for containing a coil spring stent. Pliers are used to facilitate the loading of the coil spring into said grooves whereupon completion of the loading of the outer cylinder is placed over the inner core thereby retaining the coil in the compressed state until the coil is released.

U.S. Pat. Nos. 4,690,684, and 4,720,176, each of which discloses a stent for aligning the ends of the vessel during anatomosis by thermal bonding. The stent comprises an integral solid of biologically compatible material to align the vessel ends together during anatomosis. Upon completion of the anastomosis the stent fully melts into the fluid flowing through the vessel. U.S. Pat. No. 4,770,176 also discloses a method of anastomosing a vessel utilizing the stent described in U.S. Pat. No. 4,690,684.

U.S. Pat. No. 4,878,906, which describes a prosthesis comprising a flexible thin-walled plastic sleeve for repairing damaged vessels. The sleeve having sufficient length to cover the damages area of the vessel forms a sealed interface on its outer peripheral ends with the inner peripheral surface of the vessel, thereby providing a bridge, bypassing the damaged area of the vessel.

U.S. Pat. No. 4,830,003, which discloses a cylindrical shaped stent comprising angled wires of biocompatible metal. The angled wires are connected obliquely at alternate ends to form a compressible open ended tube.

U.S. Pat. No. 4,866,062, which discloses a radially expandable coronary stent. The stent comprises a flat expandable wire band which is preformed in a zigzag pattern to provide expansion capability. The band which is wound into a cylindrical shape is inflated by means of a variable diameter device. The band expands radially exhibiting a cylindrical shape with increasing diameter.

U.S. Pat. Nos. 4,800,882, 4,739,762 and 4,733,665, each of which discloses an expandable intraluminal graft. These grafts are made of wire or a thin balled tubular member and can be expanded by an angioplasty balloon associated with a catheter.

U.S. Pat. No. 4,760,849, which discloses a planar blank which may be made into a helical coil spring stent.

U.S. Pat. No. 4,665,918, which describes a system and method for implanting a generally tubular prothesis member having an unobstructed central passageway into the length of a blood vessel. The prosthesis member contracts to a smaller dimension for delivery through the unobstructed portion of the blood vessel, and is outwardly expansible in the blood vessel. The prosthesis member is positioned in a contracted condition between a delivery catheter and outer sheath, and expands outwardly in response to the removal of the sheath.

None of the aforegoing patents, however, disclose an anti-thrombogenic stent which decreases turbulence and improves hydraulic flow of blood therethrough. Accordingly, there remains a need for such a device.

SUMMARY OF THE INVENTION

It is an object of the present invention to provide an improved intravascular stent, whereby the intravascular stent decreases the turbulence and improves the hydraulic flow of the blood through the vessel, thus, reducing the possibility of transluminal or "out flow turbulence" thrombus developing in conjunction with the implanted stent.

Another object of the present invention is to provide an intravascular stent that satisfies the electrochemical laws for thrombosis while exhibiting limited corrosion over the duration of stent life.

The improvements of this invention over the prior art devices are the ability of the present invention to decrease the turbulence of blood flow and to improve the hydraulic flow of the blood through the vessel.

These improvements are achieved in an antiturbulent, anti-thrombogenic intravascular stent comprising a helically shaped strip of predetermined thickness of a non-thrombogenic material capable of assuming a contracted position for insertion into a blood vessel and expansible to a normally expanded position having a first end, a second end, an outer surface in contact with the blood vessel for urging the blood vessel outwardly, and an internal surface in contact with blood passing therethrough from the first end to the second end. The stent internal surface includes an airfoil for increasing the velocity of blood flow through the stent without creating areas of stagnant or turbulent flow therein or adjacent thereto.

A preferred material for the stent is titanium or aluminum and an airfoil may be formed on the strip of non-thrombogenic material by including a leading edge and a trailing edge connected by a smooth transition area therebetween across the width of the strip, with the height of the leading edge being greater than that of the trailing edge. Alternatively, the airfoil can be formed by providing the predetermined thickness of the strip at the first end to be greater than the predetermined thickness of the strip at the second end, with the predetermined thickness of the strip between the first and second ends gradually diminishing to form a relatively smooth transition therebetween.

DETAILED DESCRIPTION OF THE INVENTION

Figures 1, 2, 3:
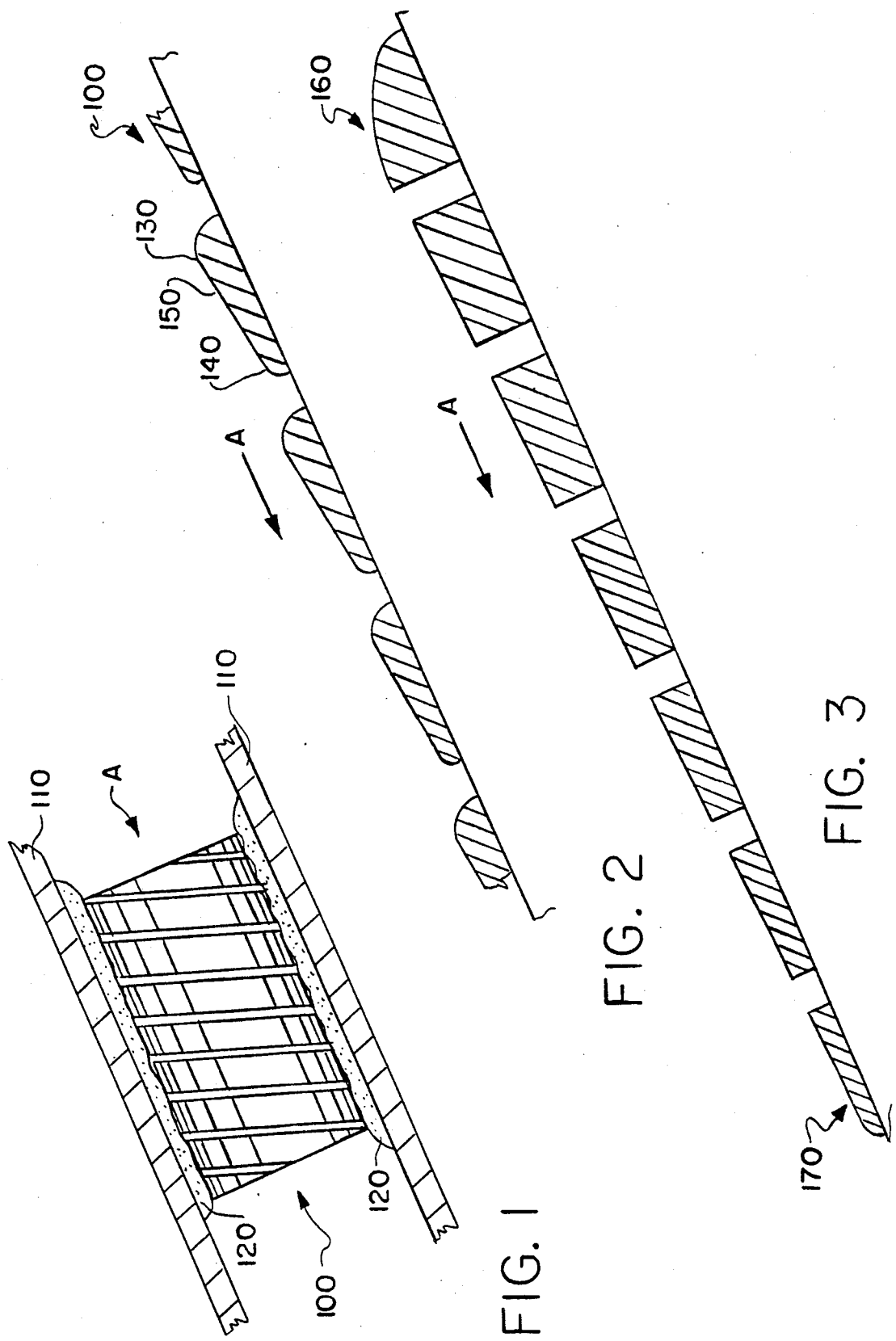
FIG. 1 is a side view of a stent in accordance with the present invention in position in a blood vessel.
FIG. 2 is an exploded view of the stent of FIG. 1 to show the airfoil surface thereof.
FIG. 3 is an exploded view of another airfoil surface for a stent according to the invention.

The stent of the present invention is preferably a titanium or aluminum air foil helix. FIG. 1 illustrates the stent 100 in position in a blood vessel 110. When implanted onto an obstruction 120 in the vessel 110, the outer surface of the stent 100 contacts the obstruction and inner surface of the vessel. The inner surface of the stent 100 allows blood to flow therethrough. Advantageously, the inner surface of the stent is shaped in the form of an airfoil. These shapes can be made by machining a flat strip of titanium or aluminum followed by configuring the machined strip in the form of a helix. The airfoil surface is achieved by configuring each stent segment to mimic the configuration of an airplane wing. Thus, each segment has a leading edge 130 of greater height than trailing edge 140, with a smooth transition 150 therebetween, as shown in FIG. 2. Thus, the thickness and cross sectional area of the stent is uniform throughout its length.

FIG. 3 illustrates an alternate embodiment of an airfoil surface for the stent of the invention. In this embodiment, the thickness of the strip at the forward end 160 of the stent is made thicker than that of the rearward end 170 of the stent. The thickness of the strip between the forward and rearward ends gradually diminishes to form a relatively smooth transition area. Thus, the overall configuration of the internal surface of the stent is similar to that of an airplane wing. The spaces between the surface segments formed by the strip do not detract from its utility of increasing blood flow velocity without creating turbulence of stagnant areas.

As the fluid in the vessel passes over the stent, the airfoil configuration increases the velocity of the blood flow therethrough in the same manner as air flows over the wing of an airplane. Blood flows in the direction of arrow A from the forward end to the rearward end of the stent. The increased velocity of the blood flow passing through said stent reduces the possibility of thrombosis because the blood flows more rapidly past the area which previously experienced the buildup or obstruction.

When a blood vessel has an obstruction, blood also flows faster as it passes the obstruction, but it produces turbulence and stagnant pools of blood distal to the obstruction. This can cause thrombus and blood element growth of the obstruction due to material depositing from the turbulent and stagnant blood pools. The present invention avoids these problems by configuring the inner portion of the stent to have an airfoil or venturi tube like surface. Thus, as blood flows by, its speed is increased and its pressure is decreased without creating turbulent or stagnant areas of blood. This higher speed, lower pressure blood flow moves rapidly past the stent, thus preventing the deposition of material therefrom. Also, the lower pressure of the blood flowing through the stent causes any material which would tend to deposit to be pulled away from the wall of the vessel where the stent is located. By use of the stent of the invention, the obstruction is removed and means are provided to prevent its regrowth.

Advantageously, the stent is formed from a thrombosis resistant material, such as titanium or aluminum, as noted above. The titanium or aluminum stent upon exposure to blood maintains a potential difference more negative than 250 millivolts versus the normal hydrogen electrode, thereby fulfilling the electrochemical laws for prevention of thrombosis. Also, titanium and aluminum stents exposed to blood deposit almost no coagulant materials, coagulant enzymes or proteins, thereby further reducing the possibility of thrombosis. In addition, metals which tend to go into solution produce cellular destruction due to tissue and cellular toxicity thereby reducing stent life. Stents of titanium, and to a slightly lesser degree aluminum, produce a non-soluble oxide on exposure to blood and tend not to go into solution, thus preventing a shortened stent life.

The stent of this invention can be inserted and be transported via a standard delivery system, such as that shown in U.S. Pat. No. 4,665,918, the content of which is expressly incorporated herein by reference thereto. Upon reaching the desired location in the damaged vessel, the outer sheath of the delivery system is removed and the stent expands radially contacting the inner walls of said vessel thereby preventing a decrease in the diameter of said vessel.

While it is apparent that the invention herein disclosed is well calculated to fulfill the objects above stated, it will be appreciated that numerous modifications and embodiments may be devised by those skilled in the art. For example, the internal surface airfoil configuration may be obtained by bending or cold forming a strip, rather than by machining such surfaces on the strip. It is intended that the appended claims cover all such modifications and embodiments as fall within the true spirit and scope of the present invention.

What is claimed is:

1. An anti-turbulent, anti-thrombogenic intravascular stent comprising a helically shaped strip of predetermined thickness of a non-thrombogenic material capable of assuming a contracted position for insertion into a blood vessel and expansible to a normally expanded position having a first end, a second end, an outer surface in contact with said blood vessel for urging said blood vessel outwardly, and an internal surface in contact with blood passing therethrough from said first end to second end, said stent internal surface forming an airfoil for increasing the velocity of blood flow through the stent without creating areas of stagnant or turbulent flow therein, wherein the predetermined thickness of the strip at the first end is greater than the predetermined thickness of the strip at said second end.

2. The stent of claim 1 wherein the non-thrombogenic material is titanium.

3. The stent of claim 1 wherein the non-thrombogenic material is aluminum.

4. The stent of claim 1 wherein an airfoil is formed on the strip of non-thrombogenic material.

5. The stent of claim 1 wherein the predetermined thickness of the strip between the first and second ends gradually diminishes from the thickness of the first end to the thickness of the second end to form a relatively smooth transition therebetween.

6. An anti-turbulent, anti-thrombogenic intravascular stent comprising a helically shaped strip of predetermined thickness of a non-thrombogenic material being capable of assuming a contracted position for insertion into a blood vessel and expansible to a normally expanded position having a first end, a second end, and outer surface in contact with an outer surface in contact with said blood vessel for urging said blood vessel outwardly, and an internal surface in contact with blood passing therethrough from said first end to said second end, said stent internal surface forming an airfoil with the predetermined thickness of the strip at said first end being greater than the predetermined thickness of the strip at said second end, and the predetermined thickness of the strip between the first and second ends gradually diminishing to form a relatively smooth transition therebetween, said airfoil increasing the velocity of blood flow through the stent without creating areas of stagnant or turbulent flow therein.

7. The stent of claim 6 wherein the non-thrombogenic material is titanium.

8. The stent of claim 6 wherein the non-thrombogenic material is aluminum.

* * * * *

UNITED STATES PATENT AND TRADEMARK OFFICE
CERTIFICATE OF CORRECTION

PATENT NO.   :   5,108,417

DATED        :   April 28, 1992

INVENTOR(S)  :   Philip N. Sayer

It is certified that error appears in the above-identified patent and that said Letters Patent is hereby corrected as shown below:

On the title page, [56] in the Sugita et al. reference:
(Nitionl Wire) should be (Nitinol Wire);

Item [56] in the Sawyer et al. reference:
*Nat. Acad. Sci.*, vol 53, No. 1, pp. 200-207 (1965) should be
*Pro. Nat. Acad. Sci.* ...;

Item [56], in the Wu et al. reference:
"Effect of Various Metal Electrode Sututes... should be
"Effect of Various Metal Electrode Sutures....

Signed and Sealed this

Twenty-fourth Day of August, 1993

Attest:

BRUCE LEHMAN

*Attesting Officer*     *Commissioner of Patents and Trademarks*